United States Patent [19]
Becker et al.

[11] Patent Number: 4,661,631
[45] Date of Patent: Apr. 28, 1987

[54] PROCESS FOR THE PREPARATION OF ACETIC ACID

[75] Inventors: Mitchell Becker, Teaneck, N.J.; Howard M. Sachs, Riverdale, N.Y.

[73] Assignee: The Halcon SD Group, Inc., Little Ferry, N.J.

[21] Appl. No.: 566,749

[22] Filed: Dec. 28, 1983

Related U.S. Application Data

[63] Continuation of Ser. No. 383,082, May 28, 1982, abandoned.

[51] Int. Cl.⁴ .................. C07C 51/12; C07C 53/08
[52] U.S. Cl. ................................ 562/519; 560/232
[58] Field of Search ............ 562/517, 519, 497, 406; 560/232

[56] References Cited

U.S. PATENT DOCUMENTS 2,650,245  8/1953  Thomas et al. ............... 562/519
4,323,697  4/1982  Rizkalla ....................... 562/517

Primary Examiner—Vivian Garner
Attorney, Agent, or Firm—Harold N. Wells

[57] ABSTRACT

Acetic acid is produced by reacting methanol with carbon monoxide in the presence of hydrogen, in the presence of a catalyst comprising a molybdenum-nickel or a tungsten-nickel cocatalyst component, in the presence of an iodide, and in the presence of a promoter comprising an organo-phosphorus compound or an organo-nitrogen compound, the ratio of the partial pressure of hydrogen to the partial pressure of carbon monoxide in the reaction zone being 0.05 to 0.4.

2 Claims, No Drawings

PROCESS FOR THE PREPARATION OF ACETIC ACID

This is a continuation of application Ser. No. 383,082 filed May 28, 1982, now abandoned.

This invention relates to the preparation of acetic acid from methanol by carbonylation.

Acetic acid has been known as an industrial chemical for many years and large amounts are used in the manufacture of various products. Proposals for producing carboxylic acids by the action of carbon monoxide upon alcohols (carbonylation) have been described, for example, in Reppe et al. U.S. Pat. No. 2,729,651 and in Holmes U.S. Pat. No. 4,133,963 and U.S. Pat. No. 4,218,340. However, such prior proposals involving carbonylation reactions have required the use of very high pressures. Carbonylation processes effective at lower pressures have also been proposed. French Pat. No. 1,573,130, for example, describes the carbonylation of methanol and mixtures of methanol with methyl acetate in the presence of compounds of Group VIII noble metals such as iridium, platinum, palladium, osmium and ruthenium and in the presence of bromine or iodine under more moderate pressures than those contemplated by Reppe et al. and Holmes. U.S. Pat. No. 3,769,329 and U.S. Pat. No. 3,772,380 produced acetic acid from the same reactants using an iridium or rhodium component with bromine or iodine. Schultz (U.S. Pat. No. 3,689,533 and U.S. Pat. No. 3,717,670) has disclosed a vapor-phase process for acetic acid production employing various catalysts comprising a rhodium component dispersed on a carrier. These lower-pressure carbonylation disclosures, however, require the use of expensive noble metals. More recently, Belgian Pat. No. 860,557 has proposed the preparation of carboxylic acids by carbonylation of alcohols in the presence of a nickel catalyst promoted by a trivalent phosphorus compound and in the presence of an iodide. In this process low pressure carbonylation is made possible without the use of a noble metal. This process is effective but there is room for improvement in terms of yields of the desired acid.

An improved process is described in the co-pending application of Nabil Rizkalla, Ser. No. 219,786, filed Dec. 24, 1980. That application discloses the preparation of acetic acid by the carbonylation of methanol in the presence of a catalyst comprising a molybdenum-nickel or a tungsten-nickel co-catalyst component in the presence of an iodide and in the presence of a promoter comprising an organo-phosphorus compound or an organo-nitrogen compound.

It is an object of the present invention to provide a further improved process embodying the carbonylation of methanol in the presence of a catalyst of the character just described.

In accordance with the invention, the surprising discovery has been made that the rate of the carbonylation reaction wherein methanol is converted to acetic acid can be increased significantly by carrying out the carbonylation with a mixture of carbon monoxide and hydrogen wherein the ratio of the partial pressure of hydrogen to the partial pressure of carbon monoxide in the reaction zone is maintained at 0.05 to 0.4, preferably 0.15 to 0.30, especially 0.2 to 0.25. Thus, in the invention process, methanol is reacted in the presence of a catalyst comprising a molybdenum-nickel or a tungsten-nickel co-catalyst component, in the presence of an iodide, in the presence of a promoter comprising an organo-phosphorus compound or an organo-nitrogen compound with a mixture of carbon monoxide and hydrogen in amounts such that the above-indicated ratio between the partial pressures of the two gases in the reaction zone lies within the values specified.

The reaction is carried out under superatomspheric pressure and, in general, a carbon monoxide partial pressure which is preferably at least 15 but less than 2,000 psi, most preferably 15 to 1,000 psi, is employed, although CO partial pressures of 1 to 5,000 or even up to 10,000 psi can also be applied. The total pressure is, of course, that which will provide the desired CO and $H_2$ partial pressure ratios and preferably it is that required to maintain the liquid phase. As is known in the carbonylation art, reaction rate increases as the CO partial pressure is increased, but it has been surprisingly discovered that, at any given CO partial pressure, the reaction rate is unexpectedly significantly further increased when hydrogen is also present in an amount such that the ratio of the partial pressure of hydrogen to the partial pressure of CO has the above-specified values. Lower ratios have no significant effect upon the reaction rate nor do higher ratios.

A wide range of temperatures, e.g., 25° to 350° C., can be used, but temperatures of 100° to 250° C. are preferably employed, and the more preferred temperatures generally lie in the range of 125° to 225° C. Lower temperatures can be used but they tend to lead to reduced reaction rates, and higher temperatures may be employed but there is no particular advantage in their use. The time of reaction is not a parameter of the process and depends largely upon the temperature employed, but typical residence times will generally fall in the range of 0.1 to 20 hours.

The final reaction mixture produced will normally contain volatile components such as hydrocarbyl iodide, unreacted alcohol and may contain the corresponding ester and/or ether, along with the product acid and these volatile components, after separation from the acid, can be recycled to the reaction. At the end of the desired residence time the reaction mixture is separated into its several constituents, as by distillation. Preferably, the reaction product is introduced into a distillation zone which may be a fractional distillation column, or a series of columns, effective to separate the volatile components from the product acid and to separate the product acid from the less volatile catalyst and promoter components of the reaction mixture. The boiling points of the volatile components are sufficiently far apart that their separation by conventional distillation presents no particular problem. Likewise, the higher-boiling organic components can be readily distilled away from the metal catalyst components and any organic promoter which may be in the form of a relatively non-volatile complex. The thus recovered co-catalyst as well as promoter, including the iodide component, can then be combined with fresh amounts of alcohol and carbon monoxide and reacted to produce additional quantities of carboxylic acid.

Although not necessary, the process can be carried out in the presence of an organic solvent or diluent. Since methanol has a relatively low boiling point, the presence of a higher-boiling solvent or diluent, preferably acetic acid, or the corresponding ester, e.g., methyl acetate, will make it possible to employ more moderate total pressures. Alternatively, the solvent or diluent may be any organic solvent which is inert in the environment of the process such as hydrocarbons, e.g., octane, benzene, toluene, xylene and Tetralin, or halogenated hydrocarbons such as the chlorobenzenes, e.g., trichlorobenzene, or carboxylic acids, or esters such as cellosolve acetate, and the like. Mixtures of solvents can also be used, such as mixtures of methyl acetate and acetic acid. The carboxylic acid, when used, should preferably be acetic acid since the preferred solvent is one that is indigenous to the system, e.g., acetic acid and/or methyl acetate. A solvent or diluent, when not an indigenous component is suitably selected which has a boiling point sufficiently different from the components of the reaction mixture so that it can be readily separated, as will be apparent to persons skilled in the art.

Most suitably the reaction is carried out in the presence of a limited amount of water, viz., in the range of 2 to 8%, preferably 4 to 6%, based on the weight of the reaction mixture. As disclosed in co-pending application Ser. No. 383081 being filed on even date herewith, now abandoned such use of water has been found to have a highly favorable effect in a system of the character with which this invention is concerned.

The carbon monoxide which is mixed with the hydrogen in the reaction zone is preferably in substantially pure form, as available commercially but inert diluents such as carbon monoxide, nitrogen, methane, and noble gases can be present if desired. The presence of such inert diluents does not affect the carbonylation reaction but their presence makes it necessary to increase the total pressure in the reaction zone in order to maintain the desired carbon monoxide partial pressure.

The co-catalyst components can be employed in any convenient form, viz., in the zero valent state or in any higher valent form. For example, the nickel and the molybdenum or tungsten can be the metals themselves in finely divided form, or a compound, both organic or inorganic, which is effective to introduce the co-catalyst components into the reaction system. Thus, typical compounds include the carbonate, oxide, hydroxide, bromide, iodide, chloride, oxyhalide, hydride, lower alkoxide (methoxide), phenoxide, or Mo, W or Ni carboxylates wherein the carboxylate ion is derived from an alkanoic acid of 1 to 20 carbon atoms such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Included among the catalyst components listed above are complexes of the metal co-catalyst components with organic promoter ligands derived from the organic promoters hereinafter described.

Particularly preferred are the elemental forms, compounds which are halides, especially iodides, and organic salts, e.g., salts of the monocarboxylic acid corresponding to the acid being produced. It will be understood that the foregoing compounds and complexes are merely illustrative of suitable forms of the several co-catalyst components and are not intended to be limiting.

The specified co-catalyst components employed may contain impurities normally associated with the commercially available metal or metal compounds and need not be purified further.

The organo-phosphorus promoter is preferably a phosphine, e.g. of the formula

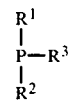

wherein $R^1$, $R^2$ and $R^3$ may be the same or different, and are alkyl, cycloalkyl, aryl groups, amide groups, e.g., hexamethyl phosphorus triamide, or halogen atoms, preferably containing 1 to 20 carbon atoms in the case of alkyl and cycloalkyl groups and 6 to 18 carbon atoms in the case of aryl groups. Typical hydrocarbyl phosphines include trimethylphosphine, tripropylphosphine, tricyclohexylphosphine and triphenylphosphine. Preferably the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexylmethylamine, 2,6-diaminopyridine, 2-quinolinol, N,N-diethyltoluamide, and imidazole.

Although generally the organic promoter is added separately to the catalyst system, it is also possible to add it as a complex with any of the co-catalyst metals, such as bis(triphenylphosphine) nickel dicarbonyl and tetrakis(triphenyl phosphite) nickel. Both free organic promoters and complexed promoters can also be used. When a complex of the organic promoter and the co-catalyst metal is used, free organic promoter can also be added.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 mol per 10 to 10,000 mols of alcohol, preferably 1 mol per 100 to 5,000 mols of alcohol and most preferably 1 mol per 300 to 1,000 mols of alcohol.

The ratio of nickel to the second co-catalyst component can vary. Typically, it is one mol of the nickel per 0.01 to 100 mols of the second co-catalyst component, preferably the nickel component is used in the amount of 1 mol per 0.1 to 20 mols, most preferably 1 mol per 1 to 10 mols of the second co-catalyst component.

The quantity of organic promoter can also vary widely but typically it is used in the amount of 1 mol per 0.1 to 10 mols of the co-catalyst components.

The amount of iodide component may also vary widely but in general, it should be present in an amount of at least 10 mols (expressed as I) per hundred mols of alcohol. Typically, there are used 10 to 50 mols of the iodide per 100 mols of alcohol, preferably 17 to 35 mols per 100 mols. Oridnarily, more than 200 mols of iodide per 100 mols of alcohol are not used. It will be understood, however, that the iodide component does not have to be added to the system as a hydrocarbyl iodide but may be supplied as another organic iodide or as the hydroiodide or other inorganic iodide, e.g., a salt, such as the alkali metal or other metal salt, or even as elemental iodine.

A particular embodiment of the catalyst comprising the molybdenum-nickel or tungsten-nickel co-catalyst component, the organic promoter component and the iodide component can be represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is an iodide source which is hydrogen iodide, iodine, an alkyl iodide wherein the alkyl group contains 1 to 20 carbon atoms or an alkali metal iodide, and Q is an organo-phosphorus compound or an organo-nitrogen compound wherein the phosphorus and the nitrogen are trivalent. Preferred are the nitrogen and phosphorus compounds previously indicated as being preferably used and in the most preferred form Q is a phosphine of the formula

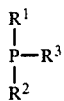

as hereinbefore defined, especially hydrocarbyl phosphines, the molar ratio of X to T being 0.1–10:1, the molar ratio of X+T to Q being 0.05–20:1 and the molar ratio of Z to X+T being 1–1,000:1.

It will be apparent that the above-described reaction lends itself readily to continuous operation in which the reactants, water and catalyst are continuously supplied to the appropriate reaction zone and the reaction mixture continuously distilled to separate the volatile organic constituents and to provide a net product consisting essentially of carboxylic acid with the other organic components being recycled and, in a liquid-phase reaction a residual catalyst containing fraction also being recycled.

The following examples will serve to provide a fuller understanding of the invention, but it is to be understood that they are given for illustrative purposes only, and are not to be construed as limitative of the invention.

EXAMPLE 1

The apparatus used in this example was a one-liter autoclave provided with an electrically-heated jacket, a magnetically driven agitator, gas and liquid feed lines, and a gas-liquid take-off line at the vapor-liquid interface. The apparatus was operated at a temperature of 210° C. and with a carbon monoxide partial pressure of 825 psi and a hydrogen partial pressure of 198 psi so that the ratio of hydrogen to carbon monoxide was 0.24. The carbon monoxide and hydrogen partial pressures were maintained by supplying these two gases continuously in the amounts required.

The feed stream, which was supplied at the rate of 720 grams/hr., consisted of a mixture of 25.2 wt. % methanol, 37 wt. % methyl iodide, 9.6 wt. % methyl acetate, 12.2 wt. % acetic acid, and 4.6 wt. % water, plus 0.2 wt. % nickel (added as nickel iodide), 0.3 wt. % molybdenum (added as molybdenum carbonyl) and 5 wt. % triphenyl phosphine.

After steady-state operation had been reached, the reaction was carried out on a continuous basis for approximately 16 hours. Analysis of the collected effluent by gas chromatography (G.C.) showed that acetic acid had been produced from methanol at the rate of 12.1 g. mol/hr/liter.

COMPARATIVE EXAMPLE A

The process and apparatus described in Example 1 were used in this experiment except that the CO pressure was 510 psi and the $H_2$ pressure was 395 psi, so that the ratio of hydrogen to carbon monoxide was 0.77. The feed stream had essentially the same composition as in Example 1 and was supplied at a rate of 540 g/hr. The effluent analysis showed that the rate at which acetic acid was produced from methanol had fallen to 6.8 g. mol/hr/liter.

COMPARATIVE EXAMPLE B

The process and apparatus described in Example 1 were again used except that the CO pressure was 1200 psi and no hydrogen was added to the system, so that the $H_2$ pressure was 0 psi. The feed stream had essentially the same composition as in Example 1 and was supplied at the rate of 300 g/hr. Effluent analysis showed that the rate at which acetic acid was produced from methanol had fallen to 3.9 g. mol/hr/liter.

What is claimed is:

1. A process for the preparation of acetic acid which comprises reacting methanol with carbon monoxide in a reaction zone in the presence of hydrogen, in the presence of a catalyst comprising a molybdenum-nickel or a tungsten-nickel co-catalyst component, in the presence of an iodide, and in the presence of a promoter comprising an organo-phosphorus compound or an organo-nitrogen compound, the ratio of the partial pressure of hydrogen to the partial pressure of carbon monoxide in the reaction zone being maintained during the reaction in the range of 0.05 to 0.4.

2. A process as defined in claim 1, wherein the ratio of the partial pressure of hydrogen to the partial pressure of carbon monoxide in the reaction zone is maintained in the range of 0.15 to 0.30.

* * * * *